(12) United States Patent
Cane' et al.

(10) Patent No.: US 12,059,550 B2
(45) Date of Patent: Aug. 13, 2024

(54) SAFETY QUICK-REFILL COMPACT PUMP FOR ADMINISTERING DRUGS

(71) Applicant: CANE' S.P.A., Rivoli (IT)

(72) Inventors: Claudio Cane', Rivoli (IT); Mario Cane', Rivoli (IT); Paolo Cane', Rivoli (IT)

(73) Assignee: CANE' S.P.A., Rivoli (IT)

( * ) Notice: Subject to any disclaimer, the term of this patent is extended or adjusted under 35 U.S.C. 154(b) by 820 days.

(21) Appl. No.: 17/253,156

(22) PCT Filed: Jun. 10, 2019

(86) PCT No.: PCT/IB2019/054805
§ 371 (c)(1),
(2) Date: Dec. 17, 2020

(87) PCT Pub. No.: WO2019/243947
PCT Pub. Date: Dec. 26, 2019

(65) Prior Publication Data
US 2021/0268177 A1    Sep. 2, 2021

(30) Foreign Application Priority Data
Jun. 18, 2018 (IT) .................. 102018000006427

(51) Int. Cl.
*A61M 5/145* (2006.01)
*A61M 5/142* (2006.01)
*A61M 5/172* (2006.01)

(52) U.S. Cl.
CPC .... *A61M 5/14566* (2013.01); *A61M 5/14248* (2013.01); *A61M 5/172* (2013.01); *A61M 2005/14573* (2013.01)

(58) Field of Classification Search
CPC ............ A61M 5/1452; A61M 5/14566; A61M 2005/14573; A61M 2005/14553
See application file for complete search history.

(56) References Cited

U.S. PATENT DOCUMENTS

| 5,269,762 A | 12/1993 | Armbruster et al. |
| 6,159,161 A * | 12/2000 | Hodosh .................. A61M 5/20 600/561 |

(Continued)

FOREIGN PATENT DOCUMENTS

EP    3257533 A1    12/2017

*Primary Examiner* — Laura A Bouchelle
(74) *Attorney, Agent, or Firm* — Howson & Howson LLP (57) ABSTRACT

A safety quick-refill compact pump for administering drugs is provided. The pump includes a motor-driven electromechanical actuator, a cylindrical container, and a hollow piercing element. The actuator causes bi-directional axial sliding of a rod that carries a pusher adapted to cause axial sliding of a plunger of the container which contains a liquid drug and is equipped, at an end thereof, with a pierceable membrane. The actuator is provided with a first connecting portion of a male-female connecting joint at least partially surrounding the rod. The container is provided with a second connecting portion of the male-female connecting joint and is firmly associated with the actuator and defines a cylindrical chamber axially extending about the sliding axis of the rod. The piercing element is oriented toward the inside of the chamber and defines a duct so that the piercing element is in fluid communication with the inside of the reservoir.

9 Claims, 7 Drawing Sheets

(56) References Cited

U.S. PATENT DOCUMENTS

| | | | |
|---|---|---|---|
| 6,447,487 | B1 | 9/2002 | Cane' |
| 7,192,416 | B1 * | 3/2007 | Lazzaro ............... A61M 5/007 |
| | | | 604/152 |
| D565,176 | S | 3/2008 | Cane' |
| 7,476,216 | B2 * | 1/2009 | Takatsuka ......... A61M 5/14546 |
| | | | 604/67 |
| D659,234 | S | 5/2012 | Cane' |
| 8,172,814 | B2 | 5/2012 | Cane' |
| 9,220,835 | B2 | 12/2015 | Cane' |
| 9,289,549 | B2 | 3/2016 | Cane' |
| 9,463,271 | B2 | 10/2016 | Cane' |
| 10,406,283 | B2 | 9/2019 | Cane' et al. |
| 2018/0185584 | A1 | 7/2018 | Cowe et al. |
| 2019/0209772 | A1 | 7/2019 | Cane' et al. |
| 2020/0016328 | A1 | 1/2020 | Cane' et al. |

* cited by examiner

SAFETY QUICK-REFILL COMPACT PUMP FOR ADMINISTERING DRUGS

TECHNICAL FIELD

The present invention relates to a safety quick-refill compact pump for administering drugs. More particularly, the present invention relates to a compact drug infusion pump of the portable type, for thanks, for example, to a holster that can be attached to an individual's body by means of a belt, a shoulder strap or the like.

PRIOR ART

Portable infusion pumps for administering drugs are known and widely used in medicine, for example for the controlled administration of insulin to diabetic patients or of various other types of drugs in the treatment of Parkinson's disease, in iron chelation therapies or in pain therapy, and others.

Known infusion pumps comprise a pusher that is axially displaceable under control of a controlled advance mechanism, which presses onto the piston of a reservoir or cartridge containing the dose of drug to be injected and removably inserted into a housing arranged in the device.

In particular, in some of the infusion pumps of the type specified above, the cartridge containing the drug is arranged frontally on the pump body and is equipped with formations that engage in a bayonet-like manner in a corresponding frontal housing of the body. The cartridge, in this case, is equipped with a piston with a removable stem that is used for aspirating the drug and then removed to allow the pump pusher, coaxial to the cartridge, to act directly onto the aforementioned piston. In particular, known devices of this type are the Crono® series pumps, produced and marketed by the Applicant.

An infusion pump can generally be filled either by means of a pre-filled drug reservoir, i.e. a reservoir originally filled with the drug, typically by the pharmaceutical company manufacturing the drug, or by means of a disposable reservoir, for example a syringe, which is filled with drug immediately before being associated with the pump, by pouring the drug from a vial or similar container.

In the case of pre-filled reservoirs, the operations that the individual or his/her assistant must perform to fill the pump and start drug administration, are considerably simplified, compared to the case where it is necessary to manually transfer the drug to prepare the syringe to be subsequently used on the pump.

The use of pre-filled reservoirs can therefore facilitate filling of the pump and starting of the infusion. Moreover, in some cases and for certain drugs, due for example to the chemical characteristics of the substance to be injected, it is necessary to use said pre-filled reservoirs, usually made of glass, and therefore it is not possible to apply the technique of transfer from said reservoir to a disposable syringe to be used on the pump.

From the above description it is clear that, in particular when pre-filled reservoirs are used, the simplicity of filling the pump constitutes a priority.

A known solution for the use of pre-filled reservoirs in infusion pumps is described for example in EP 3257533.

According to prior art, the pre-filled drug reservoir must be inserted into the housing through the opening provided at one of the bases of the housing, then the opening is closed with a removable lid which can include a piercing element. When the lid does not include the piercing element, it is necessary to insert a separate piercing element, generally through the opposite base of the housing from which the reservoir was inserted.

From the above it is clear that the current solutions can determine at least two kinds of drawbacks. A first drawback is determined by the fact that the pump filling operations are complex and difficult to complete, especially for elderly individuals or individuals with joint difficulties. The aforementioned operations are also long to be carried out and it is desired to have a filling system that is safe and reliable, while being as fast as possible. All this also to encourage the autonomous use of the aforementioned pumps by patients who currently need assistance staff for refilling. A second drawback is determined by the fact that the engagement of the piercing element, both when said element is integrated in the lid of the housing and when it is separated therefrom and placed at the opposite base of the lid, can be difficult and the result can be imperfect. The inaccurate insertion of the piercing element, for example caused by the oblique entry of the pointed part, or tip, with respect to the pierceable membrane closing the reservoir, can disadvantageously cause radial tearing of the membrane, with consequent drug release. In this regard, it should be remembered that inside the reservoir, during normal use of the pump, a considerable pressure is generated which, though necessary, on the one hand, for the drug to escape through the piercing element, can cause, on the other hand, drug leakages when the tightness of the parties involved is not optimal.

A first object of the invention is therefore to overcome the aforementioned drawbacks by providing a compact pump for administering drugs which allows quick and safe refilling.

Another object of the invention is to provide a pump of the aforementioned type, which is also suitable for use by people with difficulties in the joints of the upper limbs or suffering from pathologies which impair coordination of movements.

Not least object of the invention is to provide a pump for administering drugs, which lends itself to be made in portable format and is therefore wearable by an individual during normal activity.

These and other objects are achieved by the safety quick-refill compact pump for administering drugs as claimed in the appended claims.

The claims form an integral part of the technical teaching herein provided in relation to the present invention.

DISCLOSURE OF THE INVENTION

The drug pump according to the invention is a compact device, which is suitable to be worn by a living being and, in particular, by a human being, for a prolonged time and during the course of the usual activities, including work. The drug pump according to the invention is advantageously provided to allow quick and safe refilling by means of a disposable reservoir containing the drug to be injected and provided with an internal sliding plunger for causing the drug to come out through the front end of the reservoir. A disposable reservoir suitable for use as a replaceable cartridge in the pump according to the invention is preferably pre-filled, i.e. it is supplied to the user already filled with the drug to be injected. Said reservoir may consist substantially of a pre-filled disposable syringe, or of a pre-filled disposable ampoule or vial provided with a sliding plunger.

Advantageously, the pump according to the invention is filled and made available for the infusion of the drug with a simple sequence of two operations of inserting the reservoir already filled with drug into the cylindrical container of the pump, and subsequently connecting the container, with the reservoir ready for use contained therein, to the pump. According to the invention, this sequence of two operations not only ensures the connection of the container and corresponding reservoir to the pump, but it also determines the fluidic connection between the volume enclosed within the reservoir and the external environment so that, by connecting, to the piercing element of the container, a cannula for a drug infusion set of a known type, one can obtain the operative configuration, ready for drug administration, without the need for further interventions by the user or his/her assistant.

According to the invention, the pump mainly comprises a motorized electromechanical actuator and a container, preferably bell-shaped, which is connectable to the actuator and is adapted to house a reservoir containing a liquid drug. The actuator is electronically controlled by a programmable electronic unit and is preferably housed within a casing further containing therein the programmable electronic unit, the electronic circuitry and the components necessary for the normal operation of the pump such as, for example, a position sensor or encoder for generating a signal indicative of the progress of the administration.

The actuator is also adapted to cause bi-directional axial sliding of an extendable sliding rod which at least partially protrudes from said casing. For determining administration of the drug contained in the reservoir housed in the container, the sliding rod carries, at its head, a pusher adapted to cause axial sliding of a plunger provided in the reservoir containing the drug. The reservoir has an open end, closed by a pierceable membrane, for example a rubber plug or the like, and is communicatable with the outside by means of a piercing element or "spike" having a through channel.

According to the invention, the actuator is further externally equipped with a first connecting portion of a male-female connecting joint. Said first connecting portion at least partially surrounds the sliding rod. Said male-female connecting joint can advantageously be a bayonet-type connecting joint, which provides for the mutual fastening of the container to the actuator by means of a first axial approaching movement and a second rotational movement.

The container of the pump comprises an elongated cylindrical body and is provided with a second connecting portion of said male-female connecting joint. Advantageously, according to the invention, the container is firmly associatable to the actuator of the pump by means of said second connecting portion complementary to the first connecting portion.

The container defines, at its inside, a cylindrical chamber which is adapted to receive therein said cylindrical reservoir containing the liquid drug and extends axially about the sliding axis of the sliding rod when said actuator and container are associated with each other. The container is further provided, at a first end thereof, with an opening as inlet for the reservoir and, at its opposite end, with a duct for transporting the drug contained within the reservoir to the outside of the container.

The pump according to the invention further comprises a hollow piercing element or "spike" oriented towards the inside of the chamber of the container and defining said duct so that, when the reservoir is housed in the chamber and the container is firmly associated with the actuator by means of the connecting joint, said piercing element is in fluid communication with the inside of the reservoir.

According to the invention, the piercing element, the container and the second connecting portion form an inseparable single body. Advantageously, in accordance with this preferred arrangement of the invention, when the body of the container is firmly associated with the body of the actuator by means of the male-female connecting joint, and the reservoir is housed in the container, the piercing element communicates, through the duct, the volume inside the reservoir and the environment outside the container. According to the invention, the piercing element, the container and the second connecting portion are made as a single piece with the technique of plastic molding.

In an embodiment variant of the invention, the container of the pump and the second connecting portion are made as a single piece with the body of the container, and the piercing element is co-molded to the body of said container.

Still according to the invention, therefore, both according to the main embodiment thereof and with the variant providing for a co-molding step, the piercing element, the container and the second connecting portion are inseparable and a separation thereof may possibly be obtained only by causing breaking of the body made of plastic material integrating said piercing element, container and second connecting portion.

Still according to the invention, said body integrating the container of the pump, the piercing element and the second connecting portion is of the disposable type, i.e. it can be used for only one administration and must be replaced for the subsequent administration. Said body, indeed, comes into contact with the drug through the piercing element and the channel provided therein and cannot be re-used if one wishes to maintain the sterilization conditions required for drug administration.

Advantageously, integrating the piercing element in the body of the container provides the advantage to facilitate piercing of the membrane of the reservoir and avoid the risk of radial tearing, which, even when small, could generate drug losses due to the considerable pressure established inside the reservoir during normal operation of the pump. The cylindrical body of the container, indeed, exerts a guiding function for the reservoir during piercing of the membrane frontally closing the reservoir, thus avoiding lateral movements or inclinations of the reservoir relative to the axis of the piercing element. In addition, this arrangement is particularly safe for the user, who does not risk to come into contact with the piercing element, as said piercing element is received on the bottom of the container.

In addition, advantageously, the pump according to the invention is operational with a reduced number of assembling operations and therefore lends itself to be used also by people with impaired mobility of the hand joints or difficulties of movement due to other pathologies.

Advantageously, the pump according to the invention does not require any preparation activity for its refilling, except the extraction of the pre-filled reservoir containing the drug from a protective casing or blister pack and the removal of a protective cap for uncovering a pierceable plug or membrane closing the reservoir.

The pump according to the invention can advantageously be used with reservoirs of any material and is particularly suitable for the use of glass reservoirs or glass vials, pre-filled with drugs, i.e. originally filled by the drug manufacturer, and having a breakable membrane made of rubber or the like, which closes a first end of the reservoir and is provided with an axially sliding rubber plunger or the like, which closes the opposite end of the reservoir. The liquid drug is therefore housed in the volume within the reservoir between the sliding plunger and the closing membrane of the front end from which the drug will exit during infusion.

According to the invention, the piercing element further comprises a connector, preferably integrated in the body of the container, at the end opposite to a piercing tip, for transferring the drug to the outside of the reservoir to a cannula connected to the piercing element by means of said connector.

Said connector may advantageously be of the luer-lock type, usually adopted for subcutaneous or Enfit™ type infusions, mainly adopted for duodenal infusions.

The programmable unit according to the invention is preferably programmed to control the operation of the actuator so as to provide a predetermined therapy, which involves infusing the drug contained in the reservoir, into the body of a living being, during a period of time and in pre-established quantities.

The housing of the actuator of the pump preferably has a substantially parallelepiped shape and is made of plastic material.

In a preferred embodiment of the invention, the pump is made in a compact and portable form, i.e. it can be worn by an individual, for example by means of a holster, a pouch, or the like, for example fastened to a belt or a shoulder strap.

According to a particular embodiment of the invention, the pump is further equipped with an adapter comprising a hollow body in which connecting portions are provided which are complementary to the connecting portions provided on the body of the actuator and on the body of the container, respectively. Said adapter advantageously allows to mount the container on a pump provided with a connecting portion which, because of its type and/or size, would not allow to receive the corresponding connecting portion provided in the body of the container. A particular case of use of the adapter occurs, for example, when a pump already available on the market and provided with a first connecting portion incompatible with the second connecting portion of the container must be equipped with a container, for example to simplify use of the pump.

Advantageously, according to this particular embodiment of the invention, the adapter includes means for firmly locking the adapter to the pump so as to allow use of the pump equipped with the adapter for a plurality of administrations with corresponding disposable containers. Preferably, according to this embodiment of the invention, the adapter is used for prolonged use and for multiple administrations. In other embodiments it will be possible to provide that the adapter is of the disposable type.

In an embodiment of the adapter, the locking means comprise a pair of screws or threaded pins radially or transversely passing through the body of the adapter and engaging in corresponding seats provided in the body of the actuator. Advantageously, according to this arrangement, the screws or threaded pins are received in cylindrical bores provided through the adapter and having a length greater than that of the screws or pins, so as to hide said screws or pins from view when completely screwed in.

Preferred embodiments of the invention are defined in the dependent claims, which are to be intended as an integral part of the present disclosure.

LIST OF FIGURES

Further features and advantages of the pump according to the invention will be more apparent from the ensuing detailed description of some embodiments of the invention, made with reference to the annexed drawings, provided merely by way of non-limiting example, in which.

DESCRIPTION OF SOME PREFERRED EMBODIMENTS

Figure 1A:
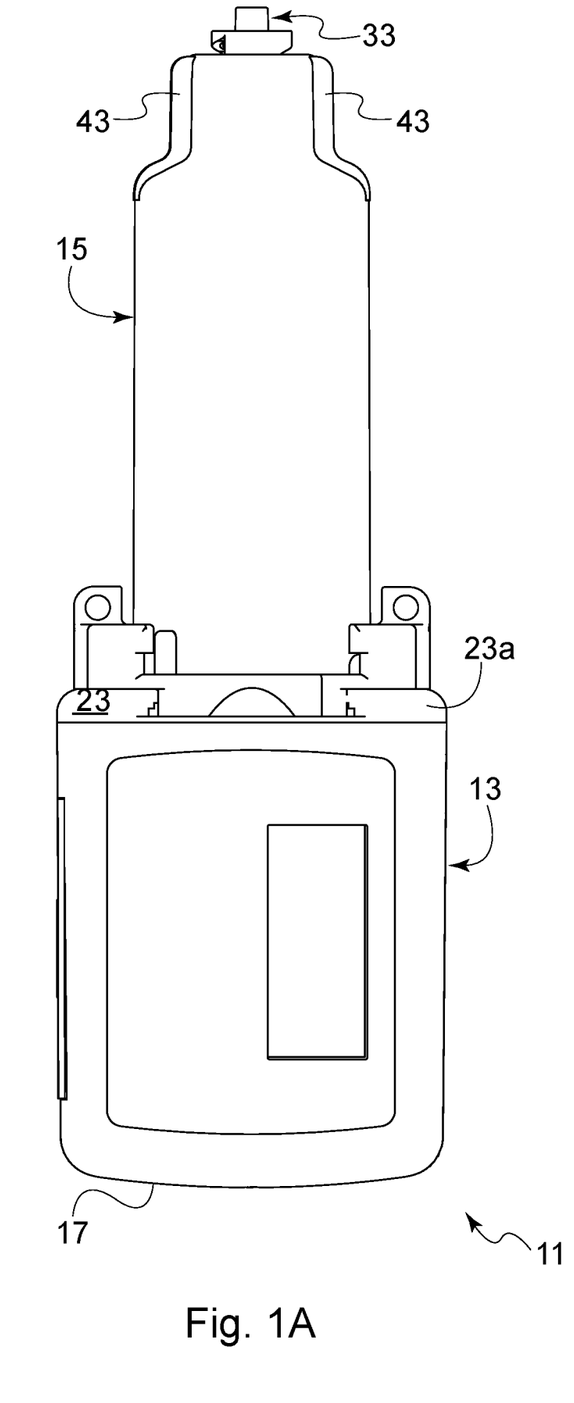
FIG. 1A is a front plan view of the pump in a preferred embodiment of the invention.
Figure 1B:
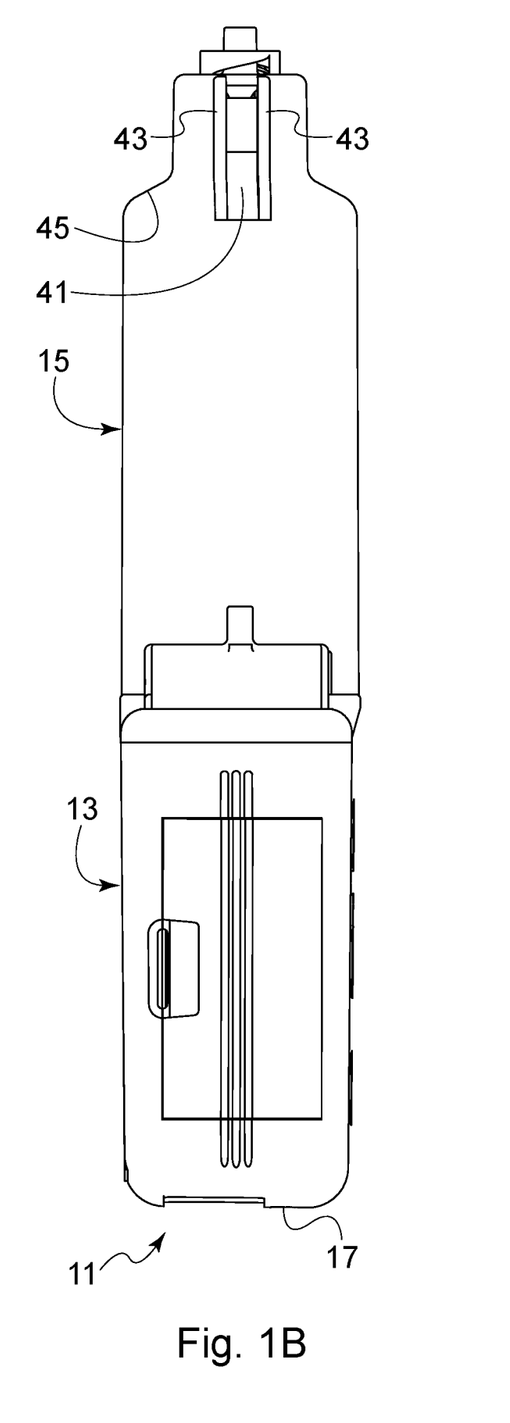
FIG. 1B is a side plan view of the pump in FIG. 1A.

Referring to FIGS. 1A and 1B, there is illustrated a pump for drugs according to a preferred embodiment of the invention. The pump according to the invention is a compact device, i.e. a device transportable or wearable by an individual, and is indicated as a whole with reference numeral 11 in the Figures.

According to the invention, the pump 11 mainly comprises a motor-driven electromechanical actuator 13 and a container 15. The container 15 is connectable to the actuator 13 and adapted to house a reservoir containing a liquid drug. The actuator 13 is electronically controlled by a programmable electronic unit and is preferably housed within a casing 17 which further contains therein the programmable electronic unit, the electronic circuitry and the components necessary for the normal operation of the pump such as, for example, a position sensor or encoder for generating a signal indicative of the progress of the administration.

The actuator 13 is also adapted to cause bi-directional axial sliding of a sliding rod which at least partially protrudes from said casing 17. For determining administration of the drug contained in the reservoir housed in the container 15, the sliding rod carries, at its head, a pusher adapted to cause axial sliding of a plunger provided in the reservoir containing the drug.

Figure 2A:
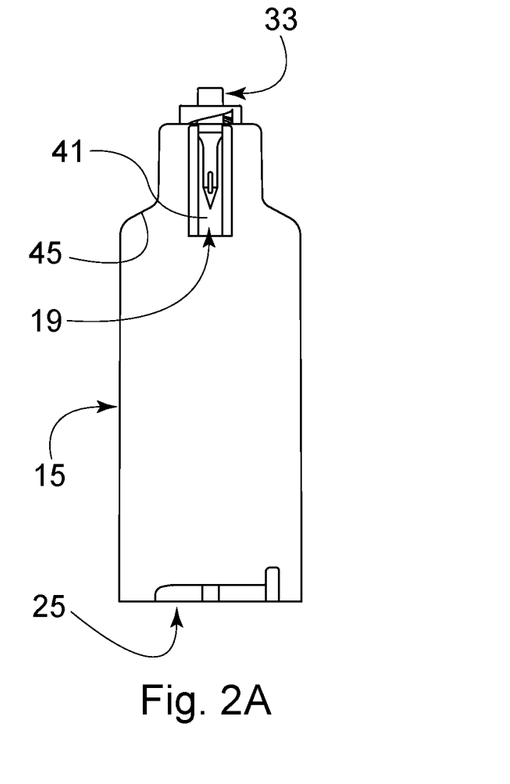
FIG. 2A is a side plan view of the container of the pump in FIG. 1A.
Figure 2B:
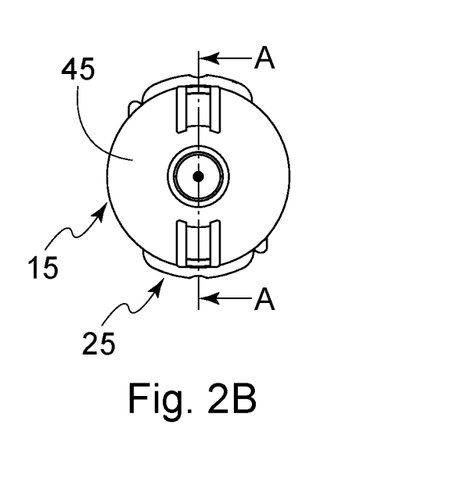
FIG. 2B is a top plan view of the container in FIG. 2A.
Figure 2C:
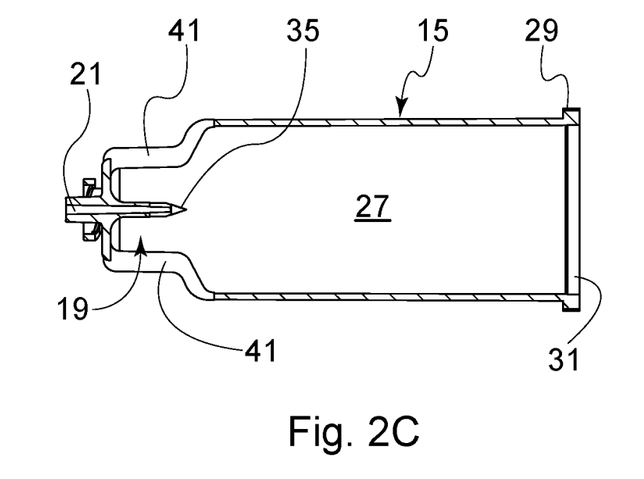
FIG. 2C is a sectional view taken along the plane A-A in FIG. 2A.
Figure 3A:
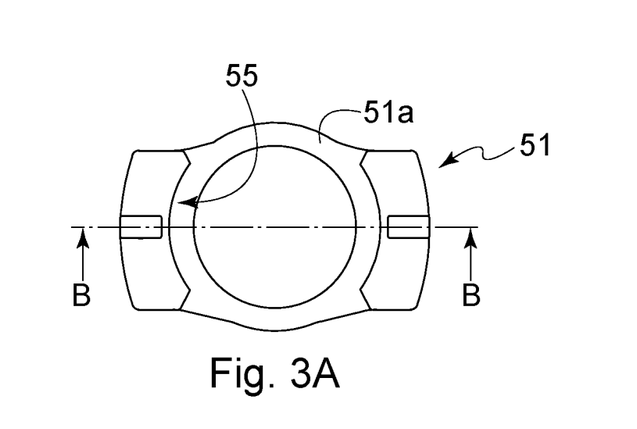
FIG. 3A is a top plan view of the adapter.
Figure 3B:
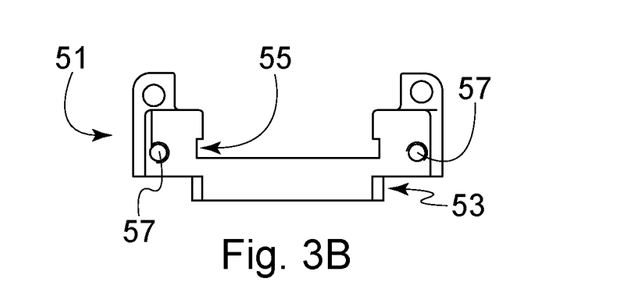
FIG. 3B is a front plan view of the adapter in FIG. 3A.
Figure 3C:
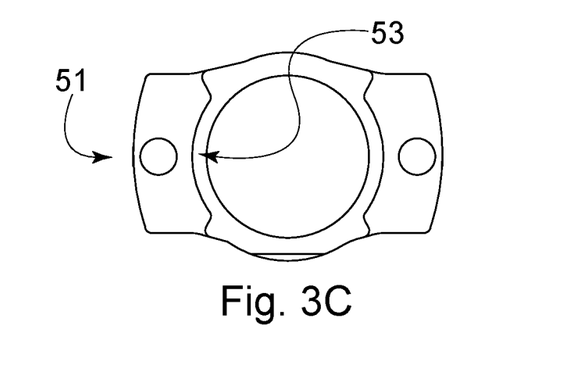
FIG. 3C is a bottom plan view of the adapter in FIG. 3A.
Figure 3D:
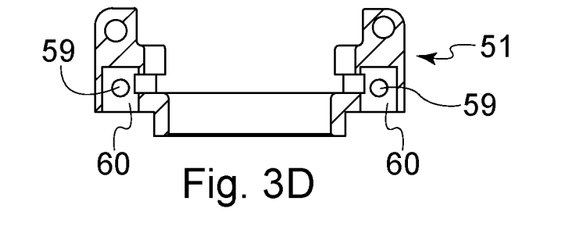
FIG. 3D is a sectional view taken along the plane B-B in FIG. 3A.
Figure 3E:
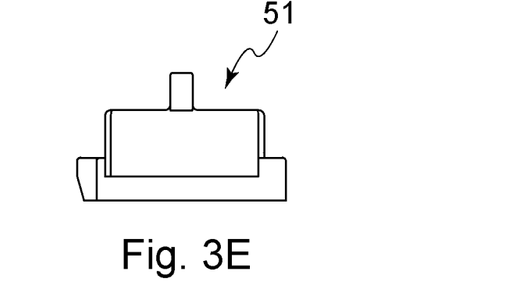
FIG. 3E is a side plan view of the adapter in FIG. 3A.

Referring also to FIGS. 2A, 2B and 2C, the reservoir has an open end, closed by a pierceable membrane, and can be put into communication with the outside by means of a piercing element or "spike" 19 having a through channel or duct 21.

According to the invention, the actuator 13 is further externally equipped with a first connecting portion 23 of a male-female connecting joint. Said first connecting portion 23 at least partially surrounds the sliding rod.

The container 15 of the pump 11 comprises an elongated cylindrical body and is provided with a second connecting portion 25 of said male-female connecting joint. Advantageously, according to the invention, the container 15 is firmly associatable to the actuator 13 of the pump 11 by means of said second connecting portion 25 complementary to the first connecting portion 23.

The container 15 defines, at its inside, a cylindrical chamber 27 which is adapted to receive therein said cylindrical reservoir containing the liquid drug. The chamber 27 extends axially about the sliding axis of the sliding rod when said actuator 13 and container 15 are associated with each other. The container 15 is further provided, at a first end 29 thereof, with an opening 31 as inlet for the reservoir and comprises, at its opposite end, the duct 21 for transporting the drug contained within the reservoir to the outside of the container 15.

The pump 11 according to the invention further comprises the hollow piercing element or "spike" 19 oriented towards the inside of the chamber 27 of the container 15 and defining said duct 21 so that, when the reservoir is housed in the chamber 27 and the container 15 is firmly associated with the actuator 13 by means of the male-female connecting joint 23,25, said piercing element 19 is in fluid communication with the inside of the reservoir by means of said duct 21.

According to a first embodiment of the invention, the piercing element 19, the container 15 and the second connecting portion 25 are made as a single piece with the body of the container 15. Advantageously, according to this arrangement of the invention, when the body of the container 15 is firmly associated with the body of the actuator 13 by means of the male-female connecting joint 23,25, and the reservoir is housed within the container 15, the piercing element 19 communicates, through the duct 21, the volume inside the reservoir and the environment outside the container 15.

According to this embodiment of the invention, the piercing element 19, the container 15 and the second connecting portion 25 are made as a single piece with the technique of plastic molding. To this aim, the body of the container 15 preferably comprises a pair of diametrically opposite windows 41 which allow to pull out a pair of sliders for molding the tip 35 of the piercing element 19. Advantageously, according to the invention, in order to counteract the weakening due to the absence of plastic material determined by the presence of the windows 41, there are provided pairs of axial ribs 43 arranged along the generatrices of the cylindrical body of the container 15. In the illustrated embodiment, the container 15 comprises a bell-shaped cylindrical body further provided with a frustoconical portion 45 at the piercing element 19. Said portion 45 acts as an abutment surface, in the chamber 27, for the reservoir containing the drug to be injected.

Still according to the invention, therefore, the piercing element 19, the container 15 and the second connecting portion 25 are inseparable from one another and a separation thereof can possibly be imagined only by causing breaking of the body of plastic material integrating said piercing element 19, said container 15 and said second connecting portion 25.

Still according to the invention, said body integrating the container 15 of the pump 11, the piercing element 19 and the second connecting portion 25 is of the disposable type, i.e. it can be used for only one administration and must be replaced for the subsequent administration. Said body of the container 15, indeed, comes into contact with the drug through the piercing element 19 and the channel 21 provided therein and cannot be re-used if one wishes to maintain the sterilization conditions required for drug administration.

Advantageously, integrating the piercing element 19 in the body of the container 15 provides the advantage to facilitate piercing of the membrane of the reservoir and avoid the risk of radial tearing, which, even when small, could generate drug losses due to the considerable pressure established inside the reservoir during normal operation of the pump 11.

In addition, advantageously, the pump 11 according to the invention is operational with a reduced number of assembling operations and therefore lends itself to be used also by people with impaired mobility of the hand joints or difficulties of movement due to other pathologies.

The pump 11 according to the invention can advantageously be used with reservoirs of any material and is particularly suitable for the use of glass reservoirs or glass vials, pre-filled with drugs, i.e. originally filled by the drug manufacturer, and having a breakable membrane made of rubber or the like, which closes a first end of the reservoir and is provided with an axially sliding rubber plunger or the like, which closes the opposite end of the reservoir. The liquid drug is therefore housed in the volume within the reservoir between the sliding plunger and the closing membrane.

According to the invention, the piercing element 19 further comprises a luer-lock connector 33, preferably integrated in the body of the container 15, at the end opposite to a piercing tip 35, for transferring the drug to the outside of the reservoir to a cannula connected to the piercing element 19 by means of said luer-lock connector 33. Said connector 33 may have other forms, for example it may be of the Enfit™ type.

The programmable unit according to the invention is preferably programmed to control the operation of the actuator 13 so as to provide a predetermined therapy, which involves infusing the drug contained in the reservoir, into the body of a living being, during a period of time and in pre-established quantities.

The housing 17 of the actuator 13 of the pump 11 preferably has a substantially parallelepiped shape and is made of plastic material.

In a preferred embodiment of the invention, the pump 11 is made in a compact and portable form, i.e. it can be worn by an individual, for example by means of a holster, a pouch, or the like, for example fastened to a belt or a shoulder strap.

As can be better appreciated with reference to FIGS. 3A to 3E, according to a particular embodiment of the invention, the pump 11 can be further equipped with an adapter 51 comprising a hollow body in which connecting portions 53,55 are provided which are complementary to the connecting portions 23,25 provided on the body of the actuator 13 and on the body of the container 15, respectively. Said adapter 51 advantageously allows to mount the container 15 on a pump 11 provided with a connecting portion 23 which, because of its type and/or size, would not allow to receive the corresponding connecting portion 25 provided in the body of the container 15. A particular case of use of the adapter 51 occurs, for example, when a pump 11 already available on the market and provided with a first connecting portion 23 incompatible with the second connecting portion 25 of the container 15 must be equipped with a container 15, for example to simplify use of the pump 11.

Advantageously, according to this particular embodiment of the invention, the adapter 51 includes means for firmly locking the adapter 51 to the pump 11 so as to allow use of the pump 11 equipped with the adapter 51 for a plurality of administrations with corresponding disposable containers. Preferably, according to this embodiment of the invention, the adapter 51 is used for prolonged use and for multiple administrations. In other embodiments it will be possible to provide that the adapter 51 is of the disposable type. The adapter 51 may advantageously be made of plastic or metal, for example aluminum.

In an embodiment of the adapter 51, the locking means comprise a pair of screws or threaded pins 57 radially or transversely passing through the body of the adapter 51 and engaging in corresponding seats provided in the body of the actuator 13, preferably at a connecting flange 23a defining the first portion 23 of the male-female connecting joint. Advantageously, according to this arrangement, the screws or threaded pins 57 are received in cylindrical bores 59 provided through the adapter and having a length greater than that of the screws or pins 57, so as to hide said screws or pins from view when completely screwed in.

The pump 11 according to the invention is advantageously suitable to be worn by a living being and, in particular, by a human being, for a prolonged time and during the course of the usual activities, including work. The drug pump 11 according to the invention is advantageously provided to allow quick and safe refilling by means of a disposable reservoir containing the drug to be injected. A disposable reservoir suitable for use as a replaceable cartridge in the pump according to the invention is preferably pre-filled, i.e. it is supplied to the user already filled with the drug to be injected.

Advantageously, the pump 11 according to the invention is filled and made available for the infusion of the drug with a simple sequence of two operations of inserting the reservoir already filled with drug into the cylindrical container of the pump, and subsequently connecting the container, with the reservoir contained therein, to the pump. According to the invention, this sequence of two operations not only ensures the connection of the container and corresponding reservoir to the pump, but it also determines the fluidic connection between the volume enclosed within the reservoir and the external environment so that, by connecting, to the piercing element, a cannula for a drug infusion set of a known type, one can obtain the operative configuration, ready for drug administration, without the need for further interventions by the user or his/her assistant.

Figure 4:
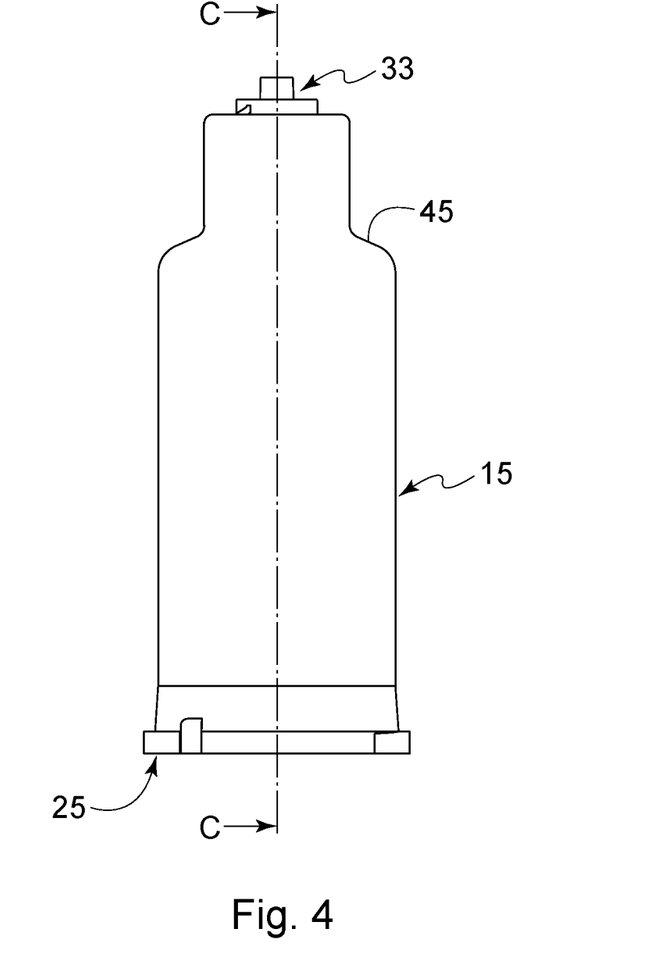
FIG. 4 is a side plan view of the container in an embodiment variant of the pump according to the invention.
Figure 5:
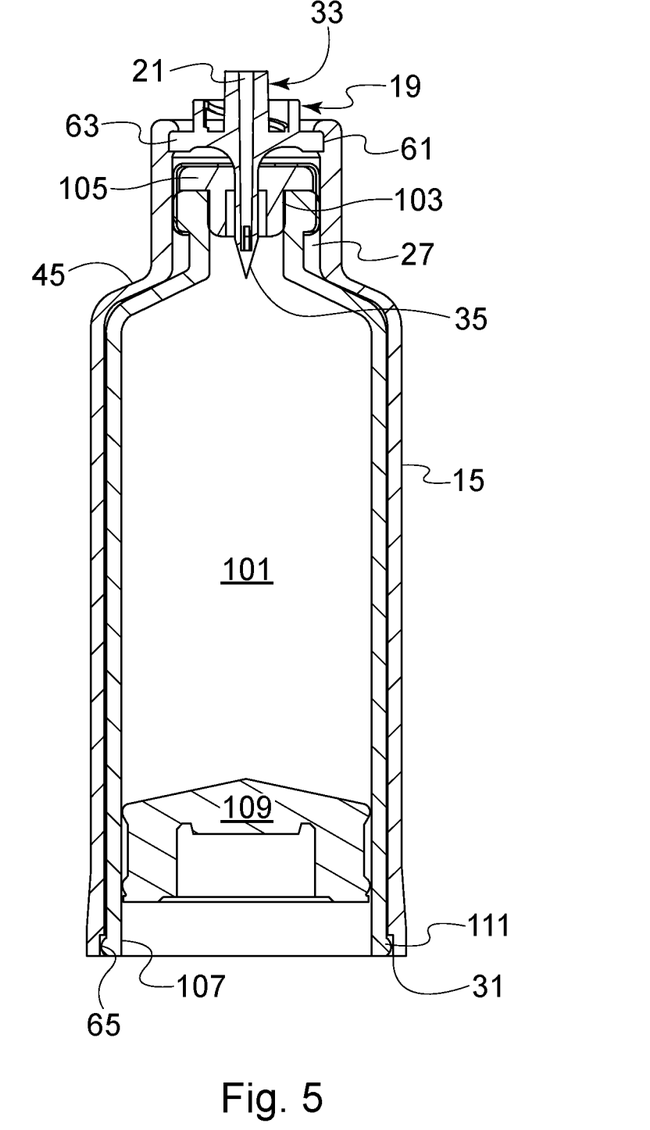
FIG. 5 is a sectional view taken along the plane C-C in FIG. 4.
Figure 6A:
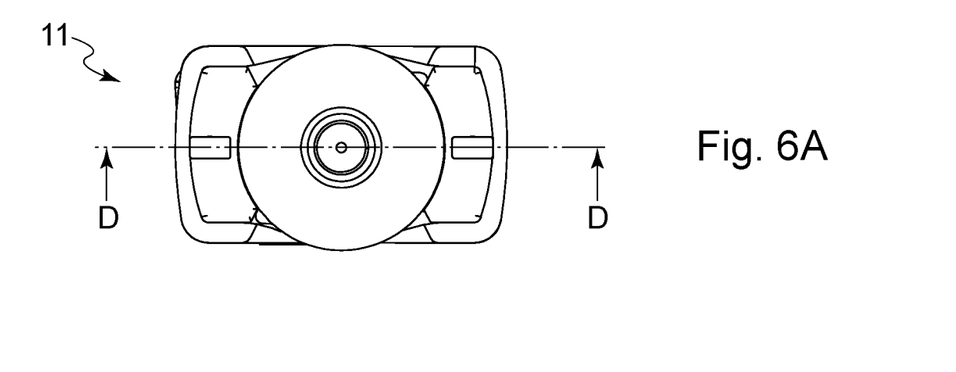
FIG. 6A is a top plan view of the pump according to the variant in FIG. 4.
Figure 6B:
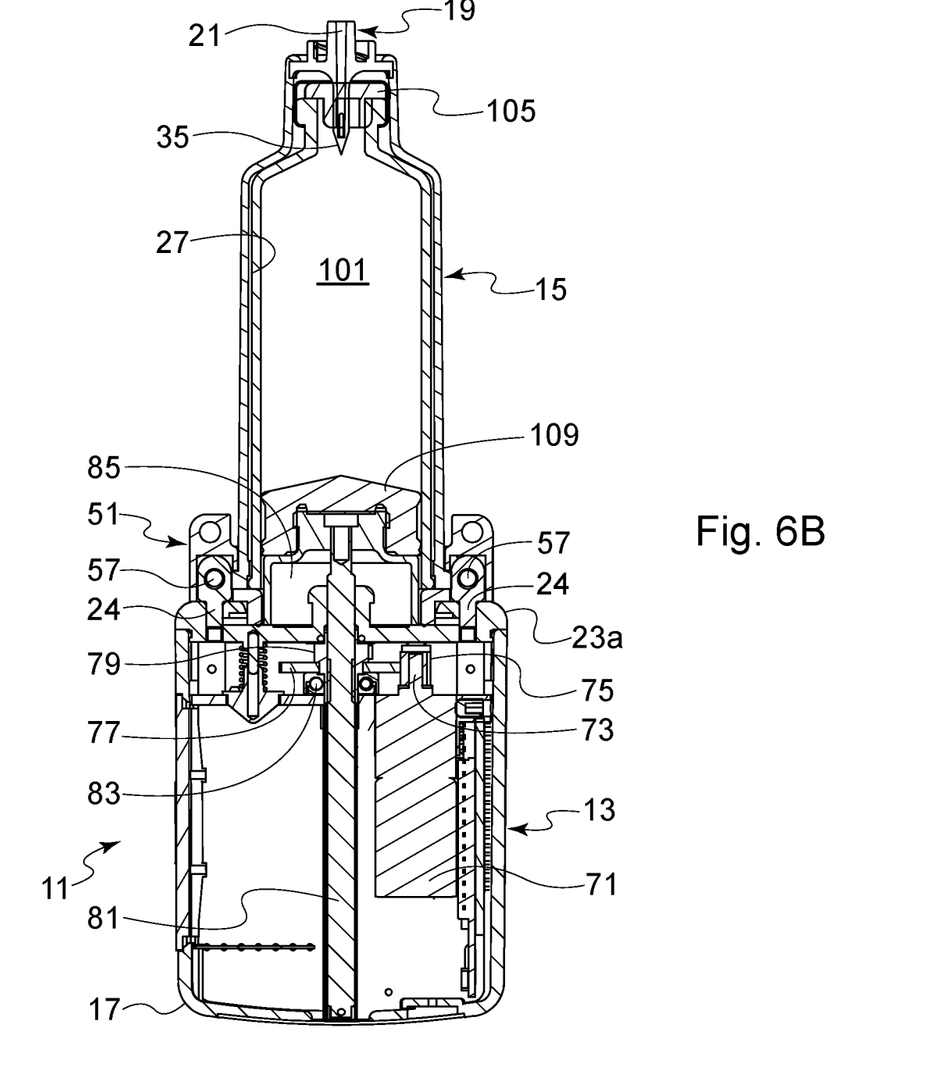
FIG. 6B is a sectional view taken along the plane D-D in FIG. 6A with the pusher withdrawn.
Figure 6C:
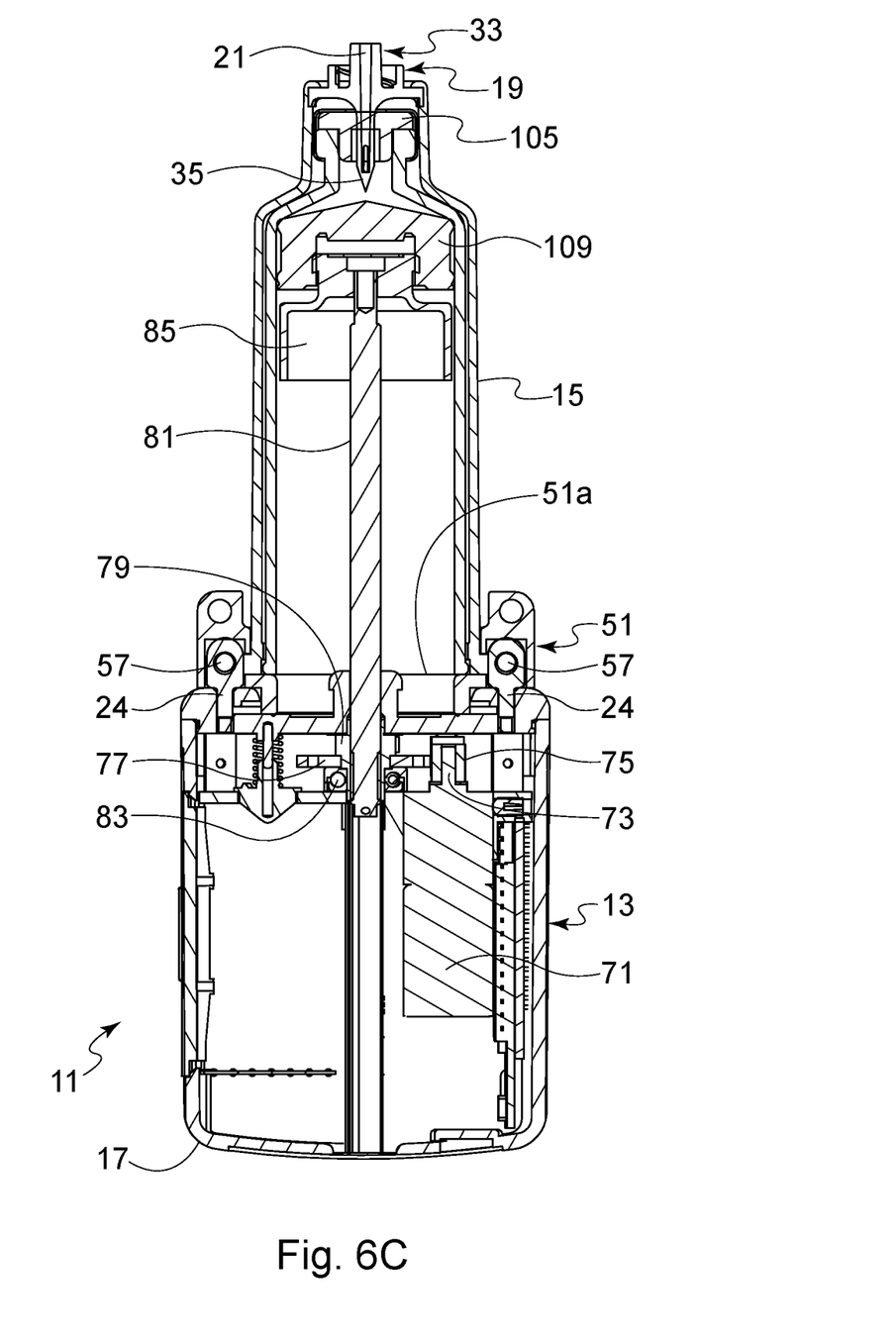
FIG. 6C is a sectional view taken along the plane D-D in FIG. 6A with the pusher advanced.

Referring to FIGS. 4 to 6, an embodiment variant of the pump 11 according to the invention will be described, in which the container 15 of the pump is made with the co-molding technique. In this embodiment variant, the remaining components of the pump 11 are substantially identical to those of the main embodiment described.

Referring in particular to FIGS. 4 and 5, the container 15 of the pump 11 defines, at its inside, a cylindrical chamber 27, which is adapted to receive therein said cylindrical reservoir 101 containing the liquid drug. The reservoir 101 is, for example, a glass vial having a first open end 103, closed by a pierceable membrane 105, and a second open end 107, closed by a sliding plunger 109. The reservoir 101 is communicatable with the outside by means of the piercing element or "spike" 19 having a through channel or duct 21 provided at the front end of the container 15.

According to this embodiment of the invention, the container 15 and the piercing element 19 form a substantially single body, being obtained with the co-molding technique, and are therefore inseparable from each other, similarly to the first embodiment described, in which said container 15 and said piercing element 19 are made as a single piece together with the second connecting portion 25.

During the co-molding step, an annular seat 61 is defined in the body of the container 15, for receiving the body of the piercing element 19 comprising a central disc-shaped part 63 formed on a plane substantially perpendicular to the channel 21 and extending radially about said channel 21. The piercing element 19 can be further provided, towards the outside, with a luer-lock connector 33, as in the illustrated embodiment intended mainly for subcutaneous administration, or a connector of a different type, for example a connector of the Enfit™ type mainly used for duodenal administration.

According to this embodiment variant of the invention, the container 15 and the piercing element 19 are made of a plastic material suitable for contact with drugs. Advantageously, according to this embodiment variant of the invention, the container 15 and the piercing element 19 are preferably made of different plastic materials, so as to meet the different constructive and functional requirements. In particular, the container 15 will preferably be made of polypropylene and the piercing element 19 will be made of polycarbonate or acrylonitrile-butadiene-styrene (ABS), which are more resistant.

The manufacturing of the container 15 of the pump 11 according to this variant of the invention preferably takes place with the following sequence of main steps. In a first step, the piercing element 19 is manufactured, preferably by molding, from a first suitable plastic material. The piercing element 19 thus obtained is then introduced into a mold for molding the container 15. A second plastic material suitable for the making of the container 15 is then injected into the mould around the piercing element 19, which is therefore imprisoned within the annular seat 61 which is formed during this molding step.

In other embodiments it is possible to provide, instead of the described piercing element, a metal needle, possibly surrounded by a plastic sleeve, co-molded with the container of the pump.

The container 15 will also preferably be made of transparent or semi-transparent plastic material and the piercing element 19 can be made opaque in a color other than that of the body of the container 15. In this way it will advantageously be possible to produce pumps 11 equipped with containers 15 provided with piercing elements 19 of different colors and differentiated according to the type of drug and, consequently, according to the type of therapy.

Referring in particular to FIGS. 6A to 6C, the operation of the pump 11 according to the invention will be described in more detail.

In FIGS. 6B and 6C, a pump 11 is illustrated provided with the container 15 made according to the described embodiment variant, which provides for the making of the body integrating the piercing element 19 and the container 15 with the co-molding technique. Apart from this difference in the making of the container 15, the other parts of the pump are identical to those of the first embodiment described, the description of which is therefore to be intended as integrated by the following.

The casing 17 of the actuator 13 houses therein an electric motor 71 which carries an input shaft 73 having a pinion 75. The pinion 75 is engaged with a toothed wheel 77 integral with an internally threaded rotary nut 79. The rotary nut 79 houses therein an externally threaded sliding rod 81 adapted to extend at least partially outside the casing 17 through the flange 23a. The nut 79 is supported in its rear part, i.e. in a position distal to the container 15 housing the reservoir 101, by a thrust bearing 83 adapted to counteract the axial forces generated during infusion of the drug. The sliding rod 81 carries at its head a pusher 85 adapted to push against the plunger 109 of the reservoir 101.

According to the invention, the reservoir 101 is firmly housed inside the container 15 with its front end in contact with the inner surface of the frustoconical portion of the container 15. The opposite end of the reservoir, at which the opening 107 for the inlet of the piston 109 is provided, rests against the base 51a of the adapter 51.

As better visible in FIGS. 6B and 6C, the pair of screws or threaded pins 57 provided in the seats 59 for firmly attaching the adapter 51 to the body of the actuator 13, engage in corresponding bores provided in a pair of inserts 24 attached to the flange 23a of the actuator 13. Said inserts 24 extend axially from the flange 23a and comprise each a bore in which a corresponding screw or threaded grain 57 engages. Referring again to FIGS. 3A to 3E, the adapter 51 comprises corresponding axial seats 60 in which the portions of the inserts 24 axially protruding outside the flange 23a are received.

FIG. 6B shows the pump 11 ready to start infusion. The reservoir 101 was previously inserted into the container 15 through the rear opening 31 provided in the container 15. During the insertion of the reservoir 101 into the container 15, the pierceable membrane or plug 105 is pierced by the tip 35 of the piercing element 19 which communicates the volume inside the reservoir and the environment outside the container through the channel 21 and the connector 33. This operation of inserting the reservoir 101 into the container 15 is extremely simple and must be substantially preceded exclusively by the arrangement of the reservoir 101 from which the protection generally provided for protecting the pierceable membrane 105 must be removed.

Referring also to FIG. 5, advantageously, according to the invention, the correct positioning of the reservoir 101 inside the container 15 is preferably established also thanks to an abutment seat 65 in which an annular edge 111 radially protruding towards the outside of the reservoir 101 is received.

When the reservoir 101 is firmly associated with the container 15 with the piercing element 19 deeply stuck in the pierceable membrane 105 and the edge 111 is received in the seat 65, the container 15 provided with the reservoir 101 is ready to be associated with the actuator 13 by means of the male-female connecting joint 23,25, thus obtaining the configuration shown in FIG. 6B.

Starting from the configuration of FIG. 6B, the electric motor 71 of the actuator 13 is operated to advance the plunger 109, thus obtaining exit of the drug through the channel 21 until the configuration shown in FIG. 6C is reached.

Although FIGS. 6B and 6C illustrate a pump 11 equipped with the adapter 51, it is evident that it will be possible to omit said adapter by appropriately dimensioning the container 15 and the corresponding male-female connecting joint 23,25 defined on the flange 23a.

Numerous variants and modifications, all falling within the same inventive concept, can be made to the invention as described and illustrated.

The invention claimed is:

1. A safety quick-refill compact pump (11) for administering drugs, comprising:
   a motor-driven electromechanical actuator (13) electronically controlled by a programmable electronic unit and adapted to cause bi-directional axial sliding of an extendable sliding rod (81) which at least partially protrudes from a casing (17) enclosing said actuator (13) and carries at its head a pusher (85) adapted to cause axial sliding of a plunger (109) of a cylindrical reservoir or container (101) containing a liquid drug and equipped, at an end thereof, with a pierceable membrane (105), said actuator (13) being further externally provided with a first connecting portion (23) of a male-female connecting joint (23,25) at least partially surrounding said sliding rod (81);
   an elongated cylindrical container (15) provided with a second connecting portion (25) of said male-female connecting joint (23,25) and firmly associatable to the actuator (13) by means of said second, complementary connecting portion (25), and defining, at its inside, a cylindrical chamber (27) axially extending about the sliding axis of the sliding rod (81) when said actuator (13) and container (15) are associated with each other, and arranged to receive within it said cylindrical reservoir (101), said container (15) being provided, at a first end thereof, with an opening (31) as inlet for the reservoir (101) and, at its opposite end, with a duct (21) for transporting the drug contained within the reservoir (101) to the outside of the container (15);
   a hollow piercing element (19) oriented towards the inside of the chamber (27) and provided with a piercing tip (35) oriented towards the inside of the chamber (27) and defining said duct (21) so that, when the reservoir (101) is housed within the chamber (27) and the container (15) is firmly associated with the actuator (13) by means of the male-female joint (23, 25), said piercing element (19) is in fluid communication with the inside of the reservoir (101), characterized in that said piercing element (19), said container (15) and said second connecting portion (25) constitute a single inseparable body so that, when the body of the container (15) is firmly associated with the body of the actuator (13) and the reservoir (101) is housed within the container (15), the piercing element (19) communicates, through the duct (21), the volume inside the reservoir (101) and the environment outside the container (15);
   wherein the piercing element (19) comprises, at an end thereof, the piercing tip (35) and, at its opposite end, a luer lock or Enfit connector (33) for transferring the drug through an axial channel providing the duct (21) to the outside of the reservoir to a cannula connected to the piercing element (19) by means of said connector (33).

2. The pump according to claim 1, wherein said piercing element (19), said container (15) and said second connecting portion (25) are made as a single piece with the body of the container (15).

3. The pump according to claim 1, wherein said container (15) and said second connecting portion (25) are made as a single piece with the body of the container (15), and wherein said piercing element (19) is co-molded to the body of said container (15).

4. The pump according to claim 1, wherein the body of the container (15) is made of plastics by means of the molding or co-molding technique.

5. The pump according to claim 1, wherein the actuator (13) is housed within a housing (31) having a substantially parallelepiped shape and made of plastic material.

6. The pump according to claim 1, wherein the container (15) has a bell-like shape.

7. The pump according to claim 1, wherein an adapter (51) is provided between the actuator (13) and the container (15).

8. The pump according to claim 7, wherein said adapter comprises a hollow body in which connecting portions (53,55) are provided complementary to the connecting portions (23,25) provided on the body of the actuator (13) and on the body of the container (15), respectively.

9. The pump according to claim 8, wherein the adapter (51) comprises a pair of screws or threaded pins (57) radially or transversely passing through the body of the adapter (51) and engaging in corresponding seats provided in the body of the actuator (13).

\* \* \* \* \*